United States Patent [19]

Drzewiecki et al.

[11] Patent Number: 5,363,855
[45] Date of Patent: * Nov. 15, 1994

[54] PRESSURE WAVEFORM MONITOR

[75] Inventors: Gary M. Drzewiecki, Princeton, N.J.;
Robert D. Butterfield, Poway, Calif.;
Edward J. Ciaccio, Cherry Hill, N.J.

[73] Assignee: Rutgers University, Pizcataway, N.J.

[ * ] Notice: The portion of the term of this patent subsequent to Oct. 13, 2009 has been disclaimed.

[21] Appl. No.: 935,064

[22] Filed: Aug. 25, 1992

Related U.S. Application Data

[63] Continuation of Ser. No. 500,063, Mar. 27, 1990, Pat. No. 5,154,680.

[51] Int. Cl.⁵ ............................................ A61B 5/02
[52] U.S. Cl. ................................... 128/672; 128/675; 128/687; 128/633
[58] Field of Search .............. 188/672, 687, 696, 691, 188/700, 633; 73/705, 715, 800; 356/32

[56] References Cited

U.S. PATENT DOCUMENTS

| | | |
|---|---|---|
| 4,269,193 | 5/1981 | Eckerle .................. 128/672 |
| 4,423,738 | 1/1984 | Newgard . |
| 4,702,758 | 11/1987 | Omura . |
| 4,713,540 | 12/1987 | Gilby et al. .............. 73/862.59 |
| 4,718,426 | 1/1988 | Russell . |
| 4,718,427 | 1/1988 | Russell . |
| 4,718,428 | 1/1988 | Russell . |
| 4,784,152 | 11/1988 | Shinoda et al. . |
| 4,799,491 | 1/1989 | Eckerle . |
| 4,802,488 | 2/1989 | Eckerle . |
| 4,836,213 | 7/1989 | Wenzel et al. . |
| 4,869,261 | 9/1989 | Penaz .................. 128/667 |
| 4,945,916 | 8/1990 | Kretschmer et al. .......... 128/671 |
| 5,154,680 | 10/1992 | Drzewiecki et al. ......... 128/672 |
| 5,201,318 | 4/1993 | Rava et al. .............. 128/665 |

FOREIGN PATENT DOCUMENTS

| | | |
|---|---|---|
| 2540987 | 8/1984 | France ................... 356/32 |
| 3150925 | 6/1983 | Germany ............... 128/687 |
| 0630525 | 9/1978 | U.S.S.R. ................ 356/32 |

OTHER PUBLICATIONS

*Non-Invasive Continuous Blood Pressure Measurement From the Finger: Optimal Measurement Conditions and Factors Effecting Reliability*, Journal of Clinical Minitoring, vol. 3, No. 1, Jan. 1987, pp. 6-13, by: Kurki, et al.

*Primary Examiner*—Lee S. Cohen
*Assistant Examiner*—Robert L. Nasser, Jr.
*Attorney, Agent, or Firm*—Dykema Gossett

[57] ABSTRACT

A pressure waveform monitor noninvasively monitors the pressure waveform in an underlying vessel such as an artery. The apparatus comprises at least one continuous, relatively thin and narrow diaphragm mounted in a housing to be placed on the tissue overlying the vessel of interest. The diaphragm is longer than the diameter of the vessel for purposely monitoring pressure in the tissue adjacent the vessel of interest. The tonometer also comprises deformation sensor means for measuring deformation of the diaphragm both over the vessel and adjacent the vessel, and signal processing means for combining the waveform of the vessel as monitored by the part of the diaphragm over the vessel with the waveforms of adjacent tissue to accurately determine the actual pressure waveform in the vessel.

8 Claims, 4 Drawing Sheets

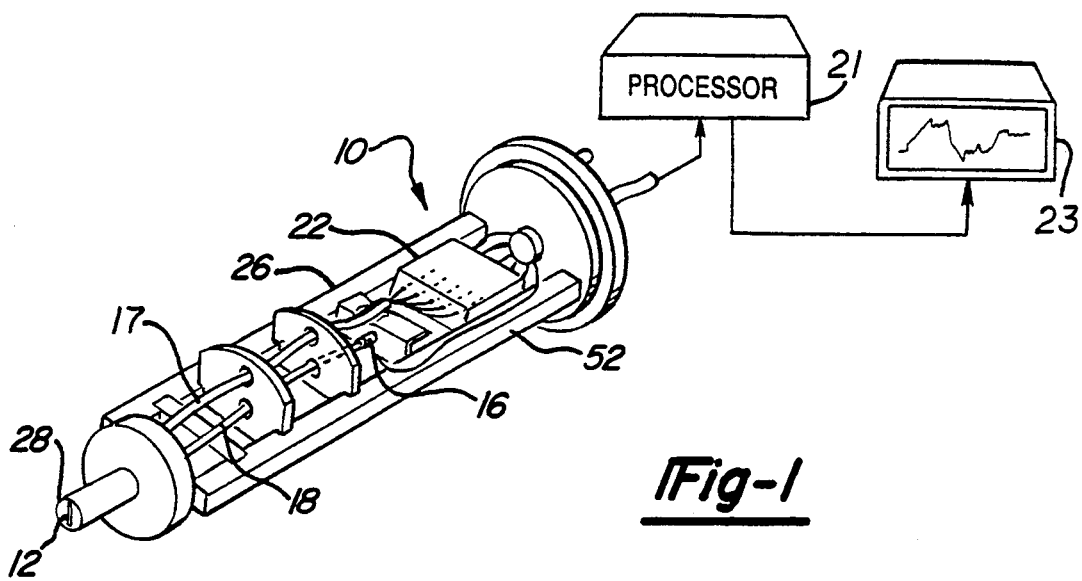
*Fig-1*
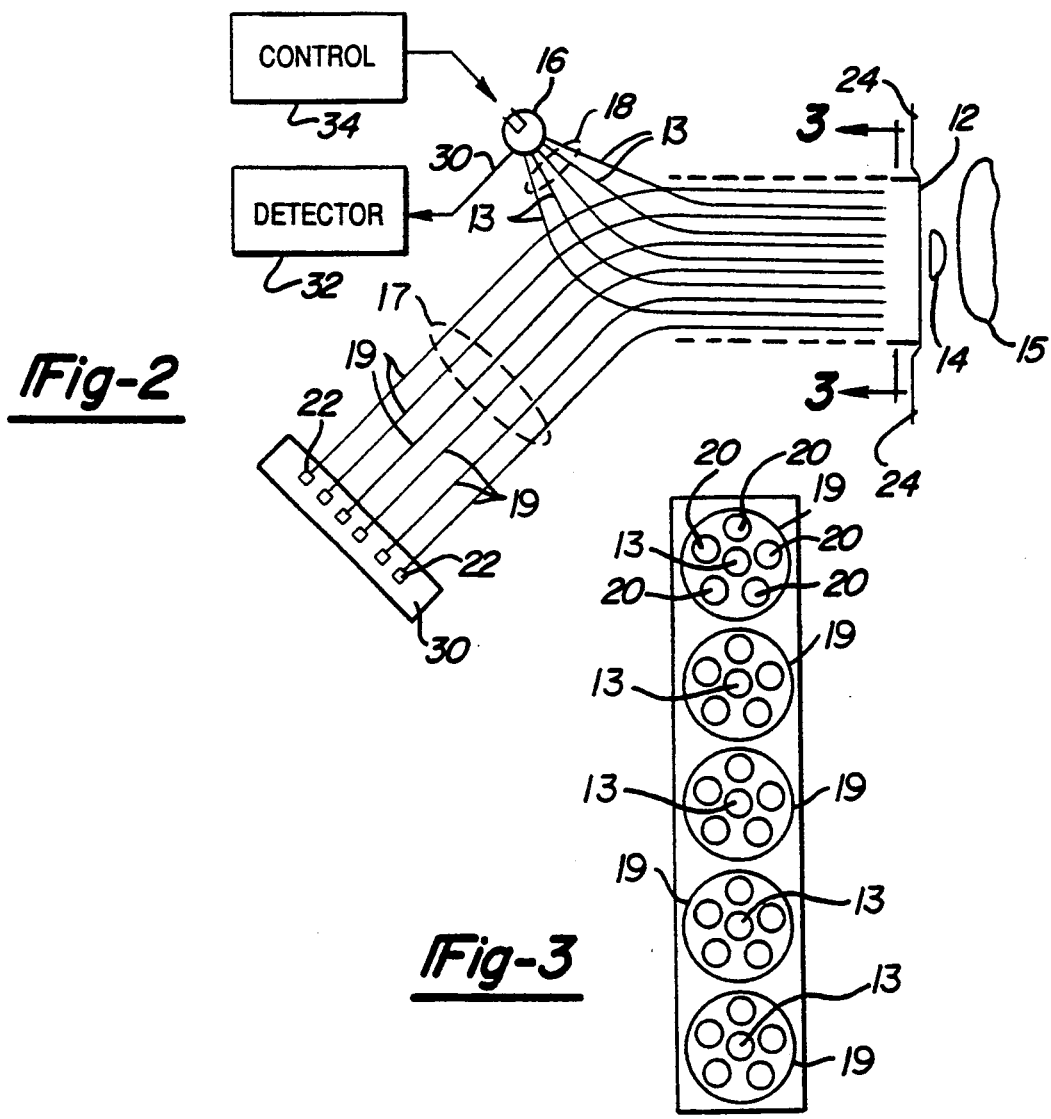
*Fig-2*
*Fig-3*

PRESSURE WAVEFORM MONITOR

This is a continuation of copending application Ser. No. 07/500,063 now U.S. Pat. No. 5,154,680 filed on Mar. 27, 1990.

BACKGROUND OF THE INVENTION

This invention relates generally to an apparatus and method for monitoring waveforms, and more particularly, to an apparatus and method for noninvasively monitoring the blood pressure waveform in a blood vessel by detection of the deformation of a diaphragm placed over tissue covering the blood vessel.

Methods for accurately monitoring the .blood pressure waveform have been under investigation for some time. While invasive methods can provide accurate waveforms, the trauma caused the patient makes the technique undesirable in many cases. One such method involves the use of a fluid filled catheter inserted into the patient's artery. While accurate blood pressure measurements can be obtained by use of this method, the negative effects on the patient may, in many cases, outweigh the accuracy in results to be obtained by use of the method.

Another method to monitor a patient's blood pressure waveform is the widely used auscultatory method of Korotkoff. This method is noninvasive; however, it only provides a measurement of systolic and diastolic pressure on an intermittent basis; it does not provide the entire waveform on a continuous basis. Furthermore, use of this method often yields inaccurate results.

The tonometric method of measuring blood pressure is noninvasive and thus an improvement over invasive techniques and in addition, it is also more accurate than the auscultatory method discussed above. Furthermore, it has the capability of providing the entire blood pressure waveform, as opposed to only the systolic and diastolic pressures provided by the auscultatory method discussed above.

In a prior type of arterial tonometer, an array of individual transducer elements is placed directly on the tissue overlying an artery or blood vessel from which blood pressure is to be determined. The elements directly sense the mechanical forces in the tissue with which each of them is in contact. The elements of the array are dimensioned and spaced apart from each other such that a plurality of these elements is required to cover the entire diameter or width of the underlying blood vessel; i.e., the size of each element is designed to cover only a small fraction of the diameter of the underlying blood vessel. The pressure of the array against the tissue is increased to properly applanate the underlying vessel but without causing occlusion. The fluid pressure within the artery is then conducted through the vessel wall and the overlying tissue to the transducers.

It has been found that with the conventional tonometer, a continuous contour of the tissue stresses under the array is not obtained due to the use of discrete elements. Additionally, it is believed that in prior methods, no compensation means is provided for motion artifacts which may affect the forces translated to the sensors from the artery.

Thus, it would be desirable to provide a tonometer system and method for monitoring the pressure in a vessel, such as an artery, which is noninvasive and is capable of faithfully transducing the vessel pressure waveform.

It would also be desirable to provide a tonometer system and method which can compensate for artifacts which may tend to decrease the accuracy of the tonometer in monitoring the waveform.

It would also be desirable to provide a tonometer system and method which has improved reliability and repeatability of pressure waveform measurements.

The present invention addresses these needs.

SUMMARY OF THE INVENTION

Briefly, and in general terms, the invention provides a noninvasive tonometer system and method for monitoring the pressure waveform in a superficial peripheral vessel such as the radial artery. The apparatus comprises a planar rigid surface in which is placed at least one thin sensing diaphragm of a narrow rectangular geometry mounted in a housing to be placed on the tissue overlying the vessel of interest. The diaphragm is longer than the diameter of the vessel for purposely monitoring pressure in the tissue adjacent the vessel of interest. The tonometer also comprises deformation sensor means for measuring deformation of the diaphragm both over the vessel and adjacent the vessel, and signal processing means for combining the waveform of the vessel as monitored by the part of the diaphragm over the vessel with the waveforms of adjacent tissue to accurately determine the actual pressure waveform in the vessel.

In a preferred embodiment, the diaphragm is formed of stainless steel and is typically of a length which is 3 to 8 times as long as the undeformed diameter of the vessel and is oriented over the vessel such that its long dimension lies perpendicular to the longitudinal axis of the vessel. The diaphragm is constructed to be thick enough to applanate the underlying vessel yet be thin enough to be deformed by stresses in the tissue with which it is in contact. The deformation of the diaphragm is small enough to prevent distortion of the tissue surface contact stress profile. Therefore, deformation of the diaphragm over its length is proportional to the stresses of the tissue with which it is in contact. The deformation of the diaphragm may be detected by optical sensing means and in one embodiment, an array of light sources and receivers is employed. Because the beams of the light sources and receivers overlap, and because the diaphragm is a single piece, a continuous, smooth curve representing the pressure waveform is provided.

The back side of the diaphragm which is not in contact with the tissue serves as a common reflector to light sources positioned in the housing. Optical fibers carry light (typically visible, infra-red or ultra-violet light) from a light source and illuminate the reflector with that light. The diaphragm reflects the light in accordance with its deformation. Other optical fibers receive the reflected light, conduct it to light transducers such as photodetectors for measurement of the amount of light received. Bundles of illuminator and receiver optical fibers are preferably arranged in rows facing the diaphragm. Based on the position of the receive optical fibers and the amount of light received, a processor provides a pressure waveform. Measurements of the deformation of the diaphragm are converted to optical signals and then to electrical signals and represent the stress in the tissue contacted. These deformation measurements are a faithful analog of the pressure waveform of the vessel.

In typical operation, the diaphragm is placed on the tissue over the radial, ulnar, superficial temporal or similar surface arteries overlaying relatively rigid structures (bone, cartilage). The diaphragm is arranged so that its approximate center is positioned over the vessel. This is accomplished by determination of which region of the diaphragm is undergoing the maximal dynamic deformation with pulsatile intraluminal pressure variations. Because the diaphragm is longer than the diameter of the vessel, the diaphragm measures the stresses in tissue areas located peripherally to the vessel. Regions of the diaphragm which cover tissue peripheral to the vessel respond to stresses in that tissue which may be caused by artifacts. These signals may be used to remove the effects of motion artifacts on the stress measurement signal of the vessel of interest. Determination of a corrected stress measurement in which the effects of small variations in applanation have been reduced is accomplished by the subtraction of a fraction of the mean lateral stresses from the stress measurements immediately over the vessel. The fraction of the lateral stress to be subtracted is continuously adjusted to minimize the noise contained in the resulting vessel signal.

The intensity of the electromagnetic energy source should ideally remain constant during measurements as well as between calibrations. In practice, however, this is difficult to achieve. Temperature changes, aging and other factors may cause variations in light intensity. A means is employed to automatically adjust the energy source intensity to lessen the possibility of measurement errors. The energy source intensity is measured directly via a path which does not involve reflection from the diaphragm. The measured output is compared to a desired level, and the difference obtained is used to automatically adjust the intensity of the source until the difference is zero. This feedback regulation ensures a stability of the energy source.

In one embodiment, additional, similarly shaped diaphragms are positioned along the vessel at sites proximal and distal to the first diaphragm. The anatomy of most vessels changes along their length and there may be a preferred position along the vessel for monitoring. The plurality of diaphragms facilitates rapid determination and maintenance of measurements from this preferred location.

Other aspects and advantages of the invention will become apparent from the following detailed description and the accompanying drawings illustrating the features of the invention by way of example.

BRIEF DESCRIPTION OF THE DRAWINGS

FIG. 1 is an illustration of a tonometer in accordance with the invention enclosed in a housing and having a continuous diaphragm;

FIG. 2 is a schematic view of a tonometer in accordance with the principles of the invention;

FIG. 3 is a schematic diagram of an example of an arrangement of bundles of fiber optic cables for use with a continuous diaphragm;

DETAILED DESCRIPTION OF THE PREFERRED EMBODIMENT

Figure 4:
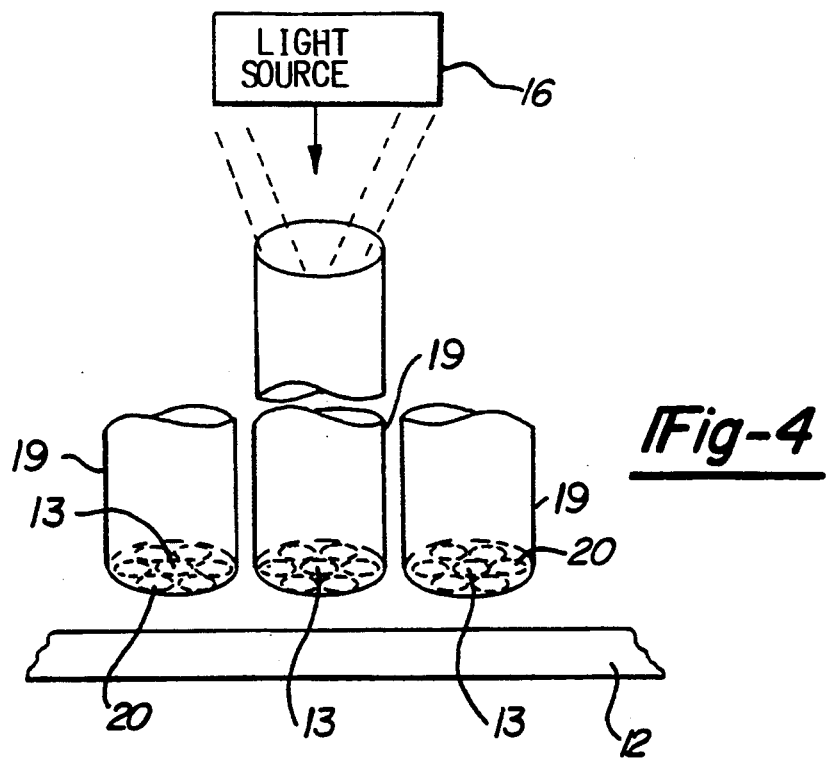
FIG. 4 is a partial view of the overlapping of the beams of optical fibers which illuminate the continuous diaphragm.

As is shown in the drawings, which are presented for the purpose of illustration only, the invention is embodied in a tonometer for noninvasively monitoring the pressure waveform in an underlying vessel of interest. Referring to FIGS. 1 and 2, the tonometer is in the form of a hand held probe 10 which preferably contains at least one generally rectangular diaphragm 12 which is to be placed over the tissue 24 overlying a vessel 14 such as an artery, and also contains means for detecting deformation of the diaphragm 12. As shown in FIG. 2, vessel 14 is disposed over an underlying, rigid bony structure 15. In one currently preferred embodiment, the diaphragm 12 is reflective, and there exists a light source 16 for providing light and a plurality of optical fibers 18 for transmitting such provided light to the reflective diaphragm 12. The tonometer also includes a plurality of groups of receiver optical fibers 17 for receiving light reflected from the reflective diaphragm 12, and light transducers, such as photo-transistors 22 for measuring the amount of light received from the diaphragm 12 and generating an electrical signal in response. The signal produced is provided to a processor 21 which in turn provides a waveform to a display 23.

Variations in the amount of light received by each group receiver optical fibers 19 are proportional to the contact tissue stresses both over and lateral to the vessel 14. These stresses correlate with systolic, diastolic and mean pressures and provide guidance for positioning of the hand held probe 10.

In applying the tonometer 10 to the tissue 24 overlying the vessel 14, enough force is used to depress and flatten the vessel 14 as shown in FIG. 2. A limited amount of vessel flattening eliminates the normal curvature of the vessel and permits translation of the fluid pressure of the vessel to the diaphragm 12. Thus, the vessel wall 14 in this region is forced to lie generally parallel to the surface of the tissue 24. The wall bending stress of the vessel is essentially eliminated so that stress sensed at the tissue surface is substantially proportional to pressure within the artery.

A tonometer made in accordance with the principles of the invention measures the stresses in the tissue overlying the vessel 14 of interest. As shown in FIG. 1, the tonometer 10 comprises a housing 26 having a surface 28 of which a portion is adapted for deformation of the tissue 24 and applanation of the vessel 14; at least one diaphragm member 12 mounted in the housing 26, adapted to be placed in contact with tissue 24 adjacent the vessel 14 and capable of being displaced in a continuous manner in response to tissue stresses adjacent the vessel 14.

The diaphragm 12 in this embodiment comprises a thin, continuous plate having a dimension which is from about 3 to about 8 times longer than the diameter of the typical vessel of interest. The diaphragm 12 is currently made of stainless steel, although it may be formed from other metals, such as aluminum, or copper, and from suitable deformable reflective plastic films or laminates or other materials. In this embodiment, the surface of the diaphragm 12 facing the optical fibers is coated to be highly reflective and thus provides a reflecting target surface for each emitter fiber 13. The optical emitter fibers 18 and the group receiver fiber 19 may be located in bundles (or groups) 19 as shown in FIG. 3. Referring to FIG. 3, bundles 19 of optical fibers are shown.

The center fiber 13 is for illumination of a portion of the diaphragm-12 while the surrounding fibers 20 are for receiving light reflected by the diaphragm 12. In another embodiment, the fiber may not be disposed in the concentric manner of FIG. 3 but may be disposed in a random manner.

Referring now to FIGS. 4, the illuminator fibers 13 provide overlapping illumination of the diaphragm 12. The light source 16 provides light to the emitter fibers 13 which transmit the illumination to the reflective diaphragm 12, which in turn reflects this illumination. The reflected illumination is received and carried through the receiver optical fibers 20 to a photodetector 22 (FIG. 2) providing a signal proportional to the light received from the reflecting diaphragm 12. The beams of the receiver fibers 20 are also overlapping. Fibers having high numerical apertures may be used to achieve this result. The signal is then received by signal processing means 21. The feature of overlapping the bundles of fibers permits increased signal to noise levels as well as a continuous, smooth curve representative of the pressure waveform.

Figure 5:
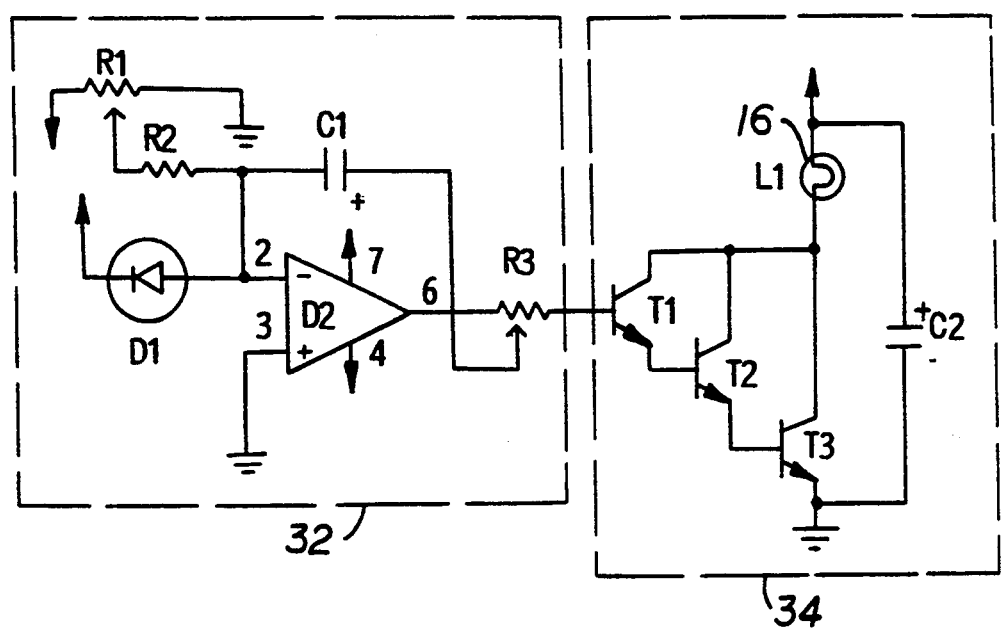
FIG. 5 is a schematic diagram of an example of a circuit usable to control the output of an incandescent light source.

Laser light, high wattage lamps and light emitting diodes may be used as alternate sources of electromagnetic radiation, although an incandescent lamp is the currently preferred light source. An incandescent lamp, although self-regulating, requires approximately 40–50 minutes to stabilize instability in the light source can result in inaccuracies in waveform readings unless a means is applied to compensate for such instabilities. Referring to FIG. 2, one means to provide control over the lamp 16 output is to use an additional optical fiber 30 to conduct the light output of the lamp directly to a detector 32 and to provide the detected signal to a lamp control 34. A feedback control circuit illustrated in FIG. 5 was implemented to regulate the lamp intensity by controlling its current. Because the lamp output is a nonlinear function, current stability is critical. To prevent oscillations, an RC-filter is provided in the error amplifier feedback circuit. This effectively maintains the lamp intensity constant with no error over a long period of time. In the embodiment shown in FIG. 5, the resistors R1 and R2 were 10 K ohms, resistor R3 was 20 K ohms, device D1 was an MRD36N, device D2 was a CA3140T, transistors T1 and T2 were 2N2222, transistor T3 was a 40409, lamp L1 was rated at 5 volt, 115 ma, capacitor C1 was 10 $\mu$F and C2 was 1000 $\mu$F.

Figure 6:
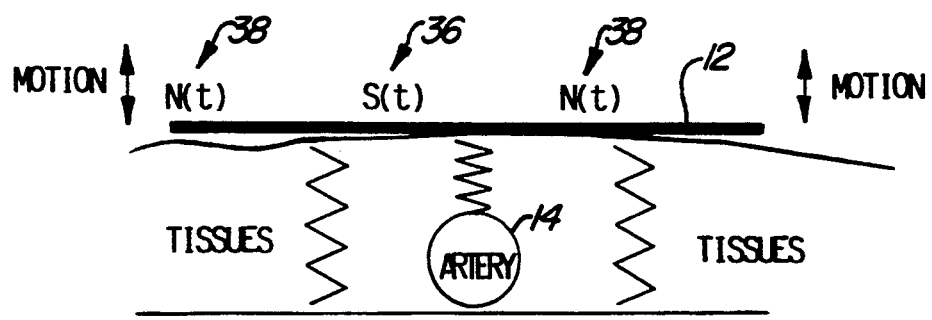
FIG. 6 is a schematic view of the function of the diaphragm in regard to tissue both over and peripheral to the vessel of interest.
Figure 7:
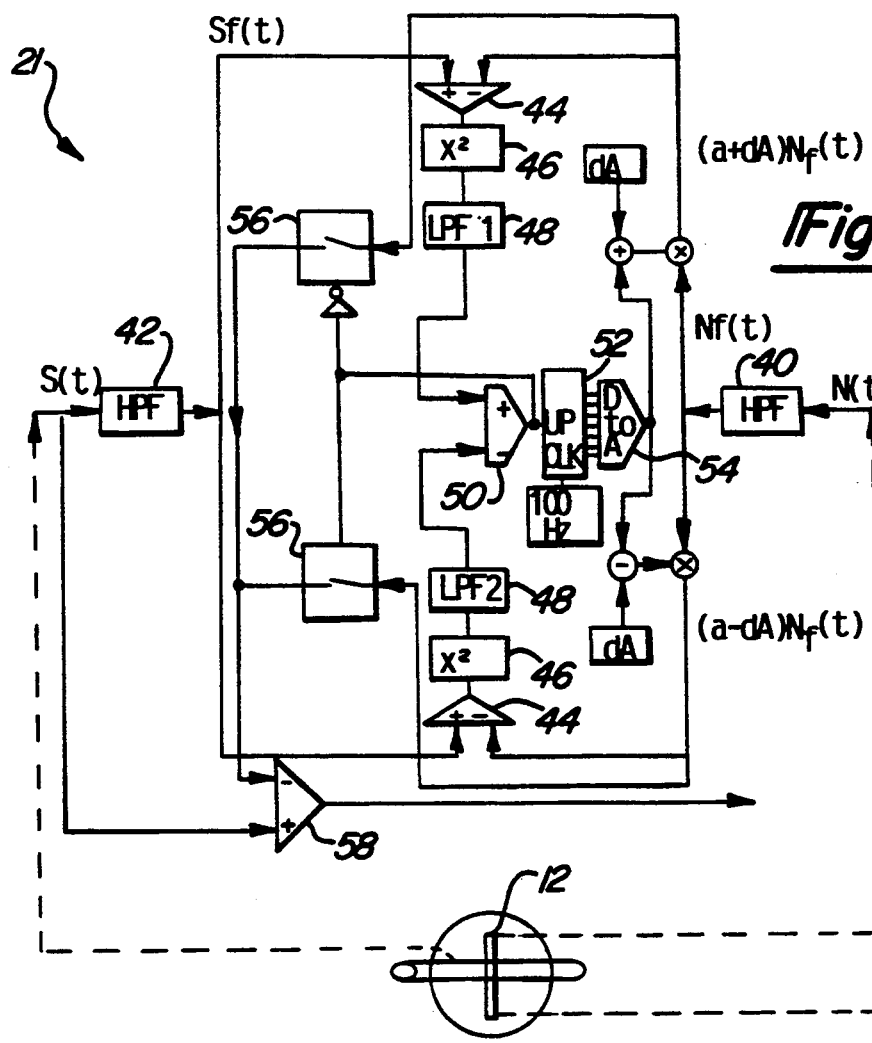
FIG. 7 is a schematic block diagram of a processing circuit usable with the diaphragm and diaphragm deformation sensors.
Figure 8:
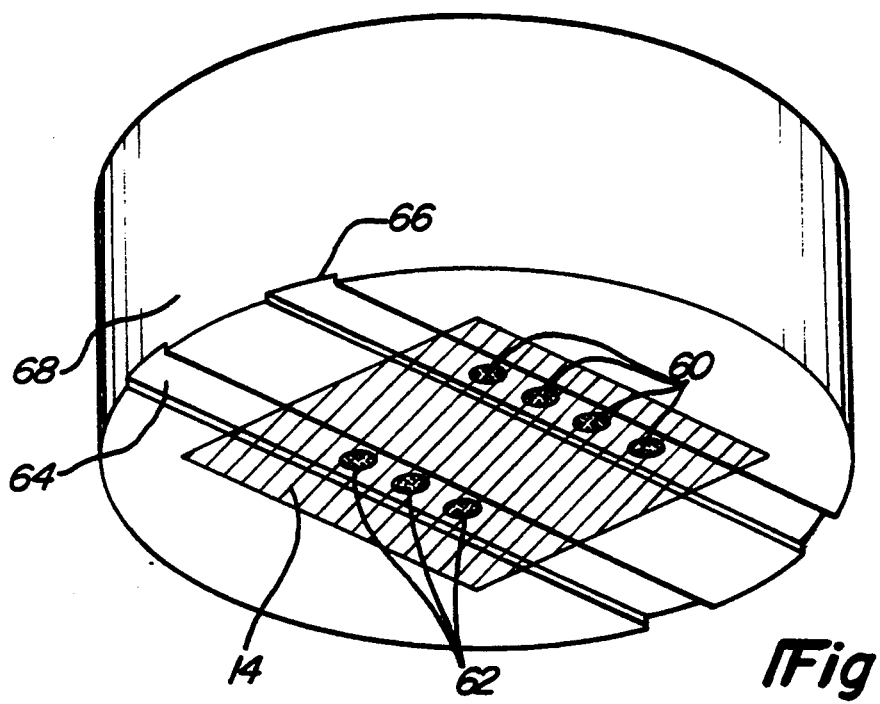
FIG. 8 is a perspective view of an alternative embodiment of the pressure sensor having two diaphragms.

Motion occurring during the pressure waveform monitoring process can produce artifacts by affecting the stresses in the tissue on which the tonometer is pressing and therefore can render pressure measurements unusable. Such motion may occur due to small variations in the displacement of the tonometer head with respect to the vessel resulting from patient or operator movement. In accordance with the principles of the invention, motion artifacts may be reduced or eliminated. Referring now to FIG. 6, a center region 36 of the diaphragm 12 can be placed generally directly over the vessel 14 of interest while the end regions 38 of the diaphragm are placed over tissue adjacent or peripheral to the vessel 14. While the central region 36 experiences vessel pressure stresses and stresses caused by motion artifacts, the end regions of the diaphragm 12 experience almost exclusively only stresses caused by motion artifacts. Although received in each region, the stresses caused by motion artifacts are not the same in each region. Therefore, motion artifact signals detected in the end regions 38 of the diaphragm 12 may be combined with the signals from the central region 36 to provide a more accurate waveform and substantially reduce the effects of patient motion. A circuit usable for such correction is shown in FIG. 7.

Because the tonometer in accordance with the invention can measure tissue contact stresses in regions both immediately over the vessel and remote from the vessel, a signal can be provided which is a combination of the pressure waveform plus the displacement noise [referred to as S(t)] and signals can be provided which represent the displacement noise alone, referred to as IN(t)]. Ideally it would be possible to simply subtract the time varying (high pass filtered) component of the noise signal [$N_f(t)$] from the pressure signal S(t) to correct for the undesired displacement variation. Thus the corrected signal would be simply:

$$P_{correct}(t) = S(t) - N_f(t)$$

In practice, the amplitude of the displacement noise generated in the tissue just over the blood vessel is different from the amplitude produced in the tissue remote from the vessel. If the relationship remained constant, then the corrected pressure could be found by:

$$P_{corrected}(t) = S(t) - A\, N_f(t)$$

where A = a constant multiplying factor

If the relationship between central and lateral motion induced noise was constant for all individuals, then a fixed coefficient "A" could be used as in the equation above. Unfortunately, the artifact pressure created in one region relative to that in another does not remain constant over time even for a given individual. Referring again to FIG. 6, the tissue is represented as a series of springs as in a mattress, the amount of force created by each spring is given simply by its displacement X times its spring constant K. In real tissue the constants for each "spring" vary with time due to factors which may include viscoelastic flow, changes in perfusion, temperature and others. Because of the variability in the relationship between the noise contained in remote regions [N(t)] and the noise component of the signal just over the vessel, it is not as accurate to simply set a single ratio factor such as "A" above to provide compensation. Thus a method to dynamically select the coefficient to be applied to $N_f(t)$ is used.

Referring now to FIG. 7, the signal from directly over the vessel 14 is indicated by S(t) and the signals from the regions remote from the region directly over the vessel are indicated by $N_f(t)$. The constant "A" is replaced by a parameter "a" which multiplies the high pass filtered 40 noise signal. The value of "a" is determined in one embodiment by the following. Firstly, the products of the scaling factor and the time varying component of the noise channel are formed:

$$(a+dA) * N_f(t) \text{ and } (a-dA) * N_f(t)$$

where dA is a selected as a constant typically less than 5% of the range of A which is 0 to 1, thus a typical dA might be 0.05. Choice of a smaller dA will result in more time being required to settle or adjust to the best value for "a" while larger values may result in less effective noise cancellation. As used herein, the symbol * indicates multiplication.

Secondly, the differences between these scaled noise signals and the time varying (mean value removed by high pass filter) component of the pulse signal $S_f(t)$ are formed such as by difference amplifiers 44:

difference signals = $S_f(t) - (a \pm dA) * N_f(t)$

Thirdly, the difference signals are squared to produce two signals proportional only to the amplitude of the differences:

squared differences = difference signals$^2$

Fourthly, the squared difference signals 46 are low pass filtered 48 using a filter whose time response spans many heartbeats.

To illustrate the operation of the system, in one case when the noise signal is zero, the filter outputs are just the high-pass filtered pulse signal (time varying part) squared and low pass filtered, the squaring operation forces the pulse signal to be uni-directional, i.e. always positive going with respect to zero. The low pass filter's effect on this signal is to find the mean value of the squared pulse signal. Thus under these conditions, the output of the two LPF1 and LPF2 are just the mean of the squared pulse signals and are the same in both inputs of the comparator 50. Under these conditions, the comparator output would switch up and down by one or two counts remaining relatively stable.

In the case when the noise signal has some finite value in both the pulse signal and noise signal channels, the differing multipliers (a+dA and a−dA) cause a larger or smaller portion of the noise energy to be added to the pulse signal. This results in one of the LPF's producing a larger average value than the other.

Fifthly, the comparator 50 causes the value of "a" to increase or decrease by means of the up/down counter 52 and the digital-to-analog converter 54 toward the value which is producing the lowest LPF output (i.e. smallest noise). As this process continues, eventually the best value of "a" is found (that is, the value producing the least mean squared error), then the direction of change of "a" is reversed because now further change of "a" in the same direction would have moved toward an increasing error. The automatic reversal occurs due to the opposite LPF producing the largest average noise level.

Sixthly, to produce a noise reduced output waveform, the original noise contaminated pulse signal from comparator 50 is combined with the best choice of "a" ±dA times the filtered noise channel signal automatically selected by one of the two switches 56 in difference amplifier 58 to result in:

$P_{out}(t) = S(t) - (a \pm dA) N_f(t)$

In this embodiment, the automatic selection of a+dA or a−dA is accomplished by use of the comparator 50 output as a control on the switches i and 2. If the comparator output is true, this indicates that LPF1 has the highest noise energy. This also means that LPF2 had the least noise (corresponding to a coefficient of a−dA) in its output. The true state of the comparator will cause the noise signal multiplied by the (a−dA) term to be added to the incoming vessel signal S(t) to obtain the most noise free output.

The fraction of the lateral stress to be subtracted is determined by continuously adjusting the fraction to minimize the noise contained in the resulting vessel signal. The optimum coefficient to use is determined by testing the performance of two slightly different coefficients in reducing the mean squared noise content of the vessel signal, then increasing or decreasing the coefficient as needed to produce the lowest mean squared noise content. The fraction of the lateral stress to be subtracted is determined by continuously adjusting the fraction to minimize the noise contained in the resulting vessel signal.

One advantage of the pressure waveform monitor in accordance with the principles of the invention is that measurement of the continuous stress contour across the tissue in the region of the vessel 14 (FIG. 2) is possible. The hand held probe 10 (FIG. 1) is positioned by the user so that the long axis of the rectangular diaphragm 12 (FIG. 2) is oriented substantially perpendicular to the axis of the vessel 14 against the tissue over the vessel and on either side of the vessel. The measurement of the continuous stress contour is preferably viewable simultaneously on a display screen 32 (FIG. 1) in an interactive mode. A specific region of the diaphragm may then be chosen to monitor blood pressure.

In one embodiment, the stainless steel diaphragm size chosen was 0.81 mm wide and 0.005 mm thick. With these dimensions and fiber-optic sensitivity data, it is predicted that the pressure sensitivity should be 3.5 mV/mmHg. All channels of the fiber deformation sensors may be recorded, input to a sample and hold analog-to-digital convertor and digitized for computer analysis.

Thus the pressure waveform monitor in accordance with the invention provides a continuous curve of the pressure waveform by using a continuous diaphragm over the vessel of interest and peripheral tissue. The monitor permits the averaging of signals by overlapping beams of the sensors to attain the continuous curve. The monitor can present not only diastolic and systolic pressures, but also the entire waveform. Means may be included in the processor to store data digitally for comparison purposes or for other manipulation.

Referring now to FIG. S, an embodiment having two sets of optical fiber bundles 60, 62 is shown. A single diaphragm 14 covers both sets. The optical fiber bundles 60, 62 are located in separate grooves 64, 66 respectively and are formed in the tonometer head 68. The use of multiple diaphragms will permit placing the tonometer head over the vessel of interest and obtaining multiple pressure waveforms along the vessel, one of which may be better than the others. It is known that the anatomy of a vessel varies along its length, such variations include thickness of overlying tissue, location and stiffness of bone, ligament, muscle and tendon under and beside the vessel and dimension of the vessel. Therefore, there may be better positions along the vessel at which to monitor pressure waveforms.

Figure 9:
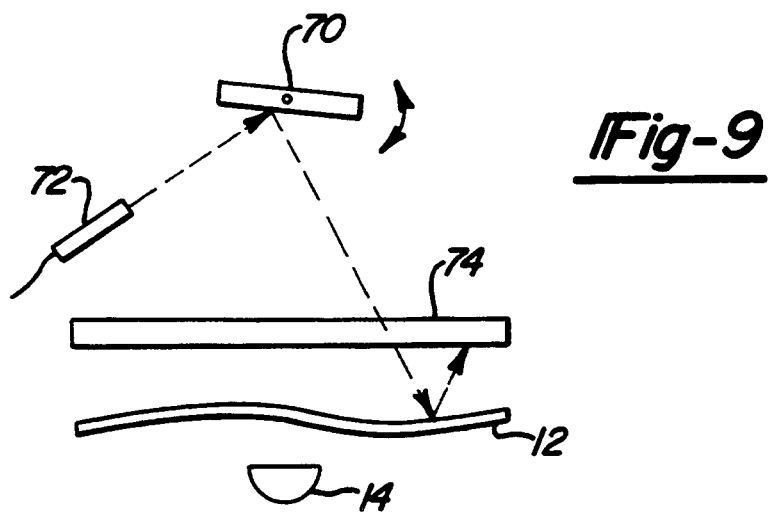
FIG. 9 is a view of an embodiment having a movable mirror for scanning the light across the reflector.

Another embodiment is shown in FIG. 9 where a movable mirror 70 is used to reflect a beam from a transmitter 72 to the diaphragm 12. The diaphragm reflects the beam to a receiver 74 which determines the intensity and position of the reflected light.

In another embodiment, the light sources and detectors can be placed immediately adjacent the diaphragm using an LED array along one row adjacent the reflective diaphragm, and a series of photodetectors in another row next to the light emitting array, to receive light reflected from the diaphragm. This approach eliminates the need for optical fibers.

While several particular forms of the invention have been illustrated and described, it will be apparent that various modifications can be made without departing from the scope of the invention. Accordingly, it is not intended that the invention be limited, except as by the appended claims.

What is claimed is:

1. A pressure waveform monitor for noninvasively monitoring the blood pressure waveform inside a blood vessel having, a lumen, comprising:
   a continuous, stress sensitive diaphragm for pressing against tissue covering the blood vessel, said diaphragm having a first length, said first length being greater than the lumen of said blood vessel, said diaphragm being continuously deformable along said first length in response to stresses in said tissue,
   sensor means displaced from said diaphragm for sensing deformations from predetermined portions along said first length of said diaphragm and for producing a vessel stress signal representing the deformation along each predetermined portion of said diaphragm, wherein said sensor means uses electromagnetic radiation reflected from said diaphragm for producing said stress signal, means for determining blood pressure from said vessel stress signal.

2. The pressure waveform monitor of claim 1, wherein said sensor means includes means for continuously sensing deformations from said predetermined portions along said first length of said diaphragm, said first length adapted to extend across said vessel and including peripheral tissue.

3. The pressure waveform monitor of claim 2, wherein said diaphragm includes a reflective surface continuously deformable along said first length, said reflective surface disposed opposite a side adapted to be pressed against said tissue, and wherein said sensor means includes means for transmitting electromagnetic radiation toward said reflective surface and means for receiving electromagnetic radiation reflected from said reflective surface and means for producing a signal representative of the amount of electromagnetic radiation received.

4. The pressure waveform monitor of claim 3, wherein said means for transmitting electromagnetic radiation transmits a wavelength selected from the group consisting of visible, infrared, and ultraviolet light.

5. The pressure waveform monitor of claim 3, wherein said means for transmitting electromagnetic radiation comprises fiber optic means for delivering energy to said reflective surface, and said means for receiving includes receiver fiber optic means for receiving energy reflected from the reflective surface.

6. The pressure waveform monitor of claim 5, wherein said fiber optic delivering means and said fiber optic receiving means are arranged in rows adjacent to said reflective surface of said diaphragm.

7. The pressure waveform monitor of claim 3, further including means for regulating the intensity of said electromagnetic radiation transmitted to said reflective surface, including a feedback loop extending between said regulating means and said means for transmitting electromagnetic radiation.

8. The pressure waveform monitor of claim 1, wherein said sensor means includes means for sweeping a beam of electromagnetic radiation across said first length of said diaphragm and means for receiving said swept beam as it is reflected from said diaphragm.

* * * * *